United States Patent
Hu et al.

(10) Patent No.: US 12,387,322 B2
(45) Date of Patent: Aug. 12, 2025

(54) APPARATUS, METHOD, AND NON-TRANSITORY COMPUTER-READABLE STORAGE MEDIUM FOR GENERATING A TASK-AWARE DYNAMIC SPARSE-VIEW SCANNING PROCEDURE

(71) Applicant: CANON MEDICAL SYSTEMS CORPORATION, Tochigi (JP)

(72) Inventors: Yi Hu, Vernon Hills, IL (US); Yu-bing Chang, Vernon Hills, IL (US); Haruki Iwai, Otawara Tochigi (JP); Joseph Manak, Vernon Hills, IL (US); John Baumgart, Vernon Hills, IL (US); James Begelman, Vernon Hills, IL (US)

(73) Assignee: CANON MEDICAL SYSTEMS CORPORATION, Tochigi (JP)

(*) Notice: Subject to any disclaimer, the term of this patent is extended or adjusted under 35 U.S.C. 154(b) by 343 days.

(21) Appl. No.: 17/940,486

(22) Filed: Sep. 8, 2022

(65) Prior Publication Data
US 2024/0087111 A1   Mar. 14, 2024

(51) Int. Cl.
*G06T 7/00* (2017.01)
*A61B 6/00* (2006.01)

(52) U.S. Cl.
CPC .......... *G06T 7/0012* (2013.01); *A61B 6/5258* (2013.01); *G06T 2207/10081* (2013.01); *G06T 2207/30168* (2013.01)

(58) Field of Classification Search
USPC ........................................................ 382/128
See application file for complete search history.

(56) References Cited

U.S. PATENT DOCUMENTS 10,438,354 B2   10/2019   Hsieh et al.
2018/0018757 A1*   1/2018   Suzuki ................... G06N 3/045
2020/0034999 A1*   1/2020   Van Heteren ......... A61N 5/1067

OTHER PUBLICATIONS

Zaech, Jan-Nico, et al. "Learning to avoid poor images: Towards task-aware C-arm cone-beam CT trajectories." International Conference on Medical Image Computing and Computer-Assisted Intervention. Springer, Cham, 2019., 9 pages.

Shen, Ziju, et al. "Learning to scan: A deep reinforcement learning approach for personalized scanning in CT imaging." arXiv preprint arXiv:2006.02420 (2020), 18 pages.

Stayman, J. Webster, and Jeffrey H. Siewerdsen. "Task-based trajectories in iteratively reconstructed interventional cone-beam CT." Proc. 12th Int. Meet. Fully Three-Dimensional Image Reconstr. Radiol. Nucl. Med (2013): 257-260, 4 pages.

* cited by examiner

*Primary Examiner* — Jacky X Zheng
(74) *Attorney, Agent, or Firm* — Oblon, McClelland, Maier & Neustadt, L.L.P.

(57) ABSTRACT

A system and method is provided for controlling an acquisition system to obtain, based on a currently acquired set of projection data, a next set of projection data that is to be acquired using a set of learned imaging conditions. The set of learned imaging conditions are, at least in part, based on training data including projection data and dose information. In one embodiment, the initial dose and angle for obtaining the initial set of projection data are chosen at random. In another embodiment, the initial dose and angle for obtaining the initial set of projection data are chosen based on a test scan and a trained neural network for outputting the initial dose and angle using a loss function.

21 Claims, 12 Drawing Sheets

APPARATUS, METHOD, AND NON-TRANSITORY COMPUTER-READABLE STORAGE MEDIUM FOR GENERATING A TASK-AWARE DYNAMIC SPARSE-VIEW SCANNING PROCEDURE

BACKGROUND

Field of the Disclosure

The present disclosure relates to improving image quality in medical imaging systems (e.g., tomosynthesis systems), and in some embodiments to improving image quality by using information about an imaging task to be performed to generate a sparse view scanning procedure.

Description of the Related Art

Medical imaging often requires a balancing between increased image quality and reduced acquisition time and/or radiation dosages. Sparse-view acquisition has great potential in terms of dose reduction and shortened acquisition times compared to convention techniques. For example, in breast cancer screening, while digital breast tomosynthesis (DBT) provides 3D information, there are dose concerns of replacing mammography with DBT. Similarly, in some interventional surgeries, some liver procedures require fast spin to reduce acquisition time which has the added benefit of reducing the use of contrast agents that could be harmful for a patient's other organs (e.g., kidneys).

Furthermore, evenly-sparsed acquisitions do not always provide the best image quality under the same amount of dose. For example, when imaging patients with metal implants, the images can contain heavier metal artefacts as opposed to a sparse-acquisition strategy that avoided the views where X-rays otherwise would have penetrated through metal. In addition, unexpected lesion features may unexpectedly appear over a certain scanning angle range during the scan. Thus, a scanning strategy planned before the scan may miss those features while those features may have been detected using a dynamic sparse-acquisition strategy.

Existing acquisition strategies also are known to optimize the image quality of each individual frame without considering the 3D image quality after reconstruction. However, improved projection domain image quality in the short-term may not necessarily optimize image quality of a 3D volume in the long-term.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to an apparatus, method, and non-transitory computer-readable storage medium for controlling an image acquisition system (e.g., a computed tomography (CT) system, a tomosynthesis system, and a C-arm CT system) to obtain projection data in a manner that reduces radiation exposure while maintaining image quality. In one such embodiment, a method for performing image acquisition control is utilized in which the method includes, but is not limited to, (a) acquiring CT volume image data; (b) extracting from the CT volume image data a plurality of simulated projections used to simulate a plurality of projection acquisitions under a set of imaging conditions simulating projection acquisitions using an image acquisition apparatus; and (c) determining a sparse subset of the plurality of simulated projections that, when reconstructed by a sparse reconstruction process, produces generated image volume data corresponding to an optimized image quality and an optimized radiation dosage. In one such embodiment, determining the sparse subset of the plurality of simulated projections includes, but is not limited to, determining the sparse subset of the plurality of simulated projections by training a first untrained machine learning system to satisfy at least one of maximizing a reward function and minimizing a loss function.

According to an embodiment, the present disclosure further relates to an image processing apparatus including processing circuitry configured to perform the above-noted image acquisition control method.

According to an embodiment, the present disclosure further relates to a non-transitory computer-readable storage medium storing computer-readable instructions that, when executed by a computer, cause the computer to perform an image acquisition control method including, but not limited to: (a) acquiring CT volume image data; (b) extracting from the CT volume image data a plurality of simulated projections used to simulate a plurality of projection acquisitions under a set of imaging conditions simulating projection acquisitions using an image acquisition apparatus; and (c) determining a sparse subset of the plurality of simulated projections that, when reconstructed by a sparse reconstruction process, produces generated image volume data corresponding to an optimized image quality and an optimized radiation dosage. In one such embodiment, determining the sparse subset of the plurality of simulated projections includes, but is not limited to, determining the sparse subset of the plurality of simulated projections by training a first untrained machine learning system to satisfy at least one of maximizing a reward function and minimizing a loss function.

According to another embodiment, the present disclosure relates to a method for determining a set of imaging conditions for an image acquisition apparatus, the method comprising: obtaining a trained neural network, the trained neural network having projection data as inputs and the set of imaging conditions as outputs, and being trained based on particular task information and/or test scan data; applying first projection data to the trained neural network to obtain a first set of imaging conditions; and obtaining the first set of imaging conditions as outputs from the trained neural network, wherein the imaging conditions include at least one of a condition of view interpolation and a condition of view extrapolation.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

The present disclosure describes a method of controlling an image acquisition apparatus so as to reduce radiation exposure while maintaining image quality at acceptable levels. One such imaging apparatus is an X-ray CT apparatus 10 illustrated in FIG. 1; however, various other imaging apparatuses can be used instead. For example, a C-arm CT system and a tomosynthesis system can be used instead and will be discussed herein with respect to addressing their limited imaging angles as compared with the illustrated CT apparatus 10.

Figure 1:
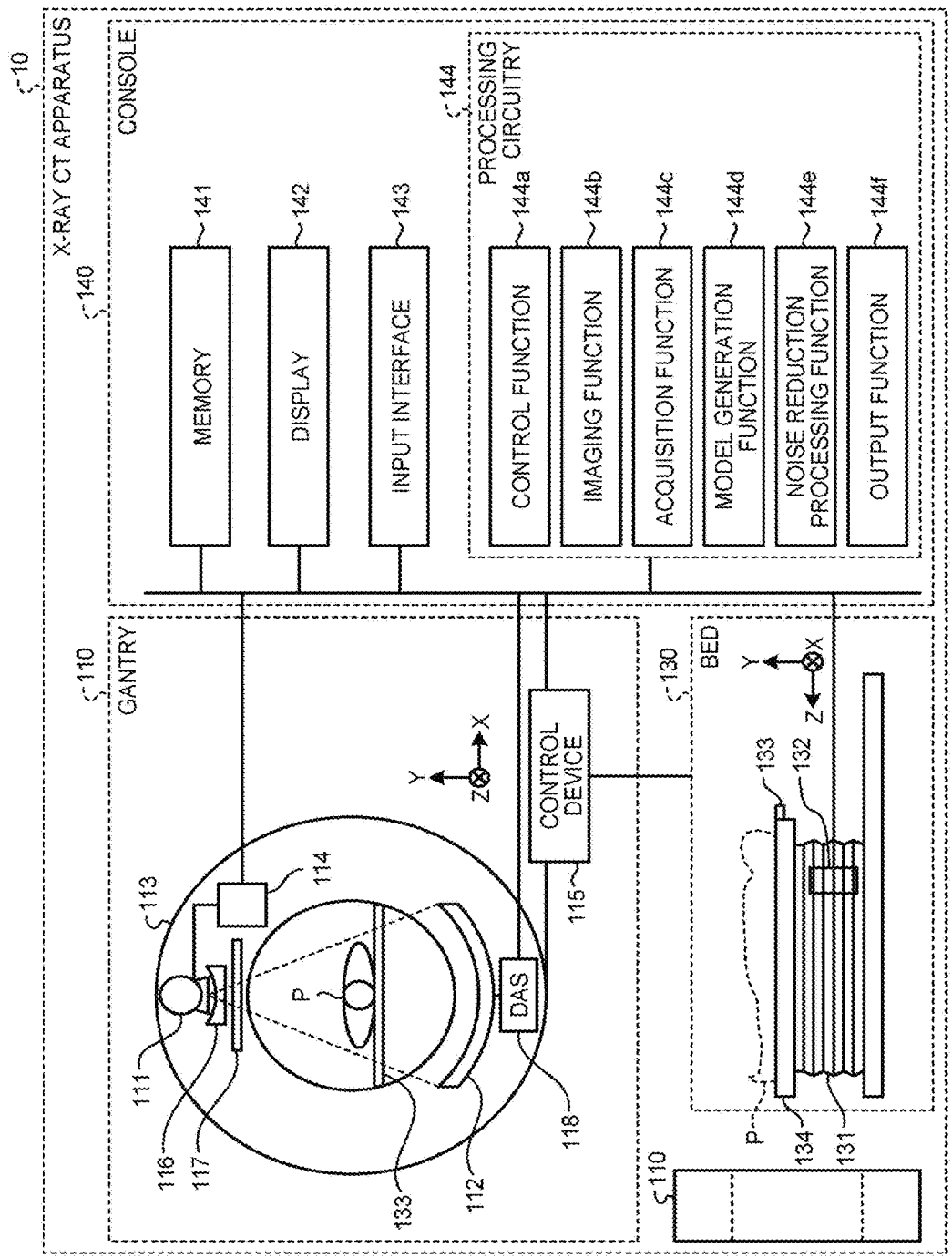
FIG. 1 is a block diagram of an exemplary configuration of an X-ray CT apparatus imaging a person as a subject according to an exemplary embodiment described below.

The illustrated X-ray CT apparatus 10 has a gantry 110, a bed 130, and a console 140. In FIG. 1, it is assumed that the longitudinal direction of a rotating shaft of a rotating frame 113 or a tabletop 133 of the bed 130 in a non-tilted state is a Z axis direction. Furthermore, it is assumed that an axial direction orthogonal to the Z axis direction and horizontal to a floor surface is an X axis direction. Furthermore, it is assumed that an axial direction orthogonal to the Z axis direction and perpendicular to the floor surface is a Y axis direction. Note that FIG. 1 illustrates the gantry 110 drawn from a plurality of directions for convenience of description and the X-ray CT apparatus 10 has one gantry 110.

The gantry 110 includes an X-ray tube 111, an X-ray detector 112, the rotating frame 113, an X-ray high voltage device 114, a control device 115, a wedge 116, a collimator 117, and a data acquisition system (DAS) 118. The X-ray tube 111 is a vacuum tube having a cathode (filament) that generates thermoelectrons and an anode (target) that generates X-rays in response to a collision of thermoelectrons. The X-ray tube 111 emits the thermoelectrons toward the anode from the cathode by the application of a high voltage from the X-ray high voltage device 114, thereby generating the X-rays to be emitted to a subject P or a phantom in the case of generating an optimized imaging protocol.

The X-ray detector 112 detects the X-rays emitted from the X-ray tube 111 and passed through the subject P (or the phantom (not shown)), and outputs a signal corresponding to the dose of the detected X-rays to the DAS 118. The X-ray detector 112, for example, includes a plurality of detection element arrays in which a plurality of detection elements are arranged in a channel direction (channel direction) along one arc centered on a focal point of the X-ray tube 111. The X-ray detector 112, for example, has a structure in which the detection element arrays with the detection elements arranged in the channel direction are arranged in a row direction (slice direction and row direction).

For example, the X-ray detector 112 is an indirect conversion type detector having a grid, a scintillator array, and a photosensor array. The scintillator array has a plurality of scintillators. Each of the scintillators has a scintillator crystal that outputs light with a photon quantity corresponding to an incident X-ray dose. The grid has an X-ray shielding plate that is disposed on the surface of the scintillator array on an X-ray incident side and absorbs scatted X-rays. The grid may also be referred to as a collimator (a one-dimensional collimator or a two-dimensional collimator). The photosensor array has a function of converting light into an electrical signal corresponding to the amount of light from the scintillator, and has, for example, photosensors such as photodiodes. Note that the X-ray detector 112 may be a direct conversion type detector having a semiconductor element that converts the incident X-rays into electrical signals.

The rotating frame 113 is an annular frame that supports the X-ray tube 111 and the X-ray detector 112 so as to face each other and rotates the X-ray tube 111 and the X-ray detector 112 by the control device 115. For example, the rotating frame 113 is a casting made of aluminum. Note that the rotating frame 113 can further support the X-ray high voltage device 114, the wedge 116, the collimator 117, the DAS 118 and the like, in addition to the X-ray tube 111 and the X-ray detector 112. Moreover, the rotating frame 113 can further support various configurations not illustrated in FIG. 1. Hereinafter, in the gantry 110, the rotating frame 113 and a part, which rotationally moves with the rotating frame 113, are also referred to as a rotating part.

The X-ray high voltage device 114 has electric circuitry such as a transformer and a rectifier, and has a high voltage generation device that generates a high voltage to be applied to the X-ray tube 111 and an X-ray control device that controls an output voltage corresponding to the X-rays generated by the X-ray tube 111. The high voltage generation device may be a transformer type device or an inverter type device. Note that the X-ray high voltage device 114 may be provided on the rotating frame 113, or may also be provided on a fixed frame (not illustrated).

The control device 115 has processing circuitry having a central processing unit (CPU) and the like, and a driving mechanism such as a motor and an actuator. The control device 115 receives input signals from an input interface 143 and controls the operations of the gantry 110 and the bed 130. For example, the control device 115 controls the rotation of the rotating frame 113, the tilt of the gantry 110, the operation of the bed 130, and the like. As an example, as control for tilting the gantry 110, the control device 115 rotates the rotating frame 113 around an axis parallel to the X axis direction based on information on an input inclination angle (tilt angle). Note that the control device 115 may be provided in the gantry 110 or may also be provided in the console 140.

The wedge 116 is an X-ray filter for adjusting the dose of the X-rays emitted from the X-ray tube 111. Specifically, the wedge 116 is an X-ray filter that attenuates the X-rays emitted from the X-ray tube 111 such that the X-rays emitted from the X-ray tube 111 to the subject P have a predetermined distribution. For example, the wedge 116 is a wedge filter or a bow-tie filter and is manufactured by processing aluminum and the like to have a predetermined target angle and a predetermined thickness.

The collimator 117 is a lead plate and the like for narrowing down the emission range of the X-rays having transmitted through the wedge 116 and forms a slit by a combination of a plurality of lead plates and the like. Note that the collimator 117 may also be referred to as an X-ray diaphragm. Furthermore, although FIG. 1 illustrates a case where the wedge 116 is disposed between the X-ray tube 111 and the collimator 117, the collimator 117 may be disposed between the X-ray tube 111 and the wedge 116. In such a case, the wedge 116 attenuates the X-rays, which are emitted from the X-ray tube 111 and whose emission range is limited by the collimator 117, by allowing the X-rays to pass therethrough.

The DAS 118 acquires X-ray signals detected by each detector element included in the X-ray detector 112. For example, the DAS 118 has an amplifier that performs an amplification process on electrical signals output from each detector element and an A/D converter that converts the electrical signals to digital signals and generates detection data. The DAS 118 is implemented by, for example, a processor.

The data generated by the DAS 118 is (1) transmitted from a transmitter having a light emitting diode (LED) provided on the rotating frame 113 to a receiver having a photodiode provided on a non-rotating part (for example, a fixed frame and the like and not illustrated in FIG. 1) of the gantry 110 by optical communication and/or (2) transmitted to the console 140. The non-rotating part is, for example, a fixed frame and the like that rotatably supports the rotating frame 113. Note that the data transmission method from the rotating frame 113 to the non-rotating part of the gantry 110 is not limited to the optical communication and may adopt any non-contact type data transmission method or a contact type data transmission method.

The bed 130 is a device that places and moves the subject P (or phantom) to be scanned and includes a pedestal 131, a couch driving device 132, the tabletop 133, and a support frame 134. The pedestal 131 is a casing that supports the support frame 134 so as to be movable in a vertical direction. The couch driving device 132 is a driving mechanism that moves the tabletop 133, on which the subject P is placed, in a long axis direction of the tabletop 133 and includes a motor, an actuator and the like. The tabletop 133 provided on the upper surface of the support frame 134 is a plate on which the subject P is placed. Note that the couch driving device 132 may also move the support frame 134 in the long axis direction of the tabletop 133 in addition to the tabletop 133.

The console 140 has a memory 141, a display 142, the input interface 143, and processing circuitry 144. Although the console 140 is described as a separate body from the gantry 110, the gantry 110 may include the console 140 or a part of each component of the console 140.

The memory 141 is implemented by, for example, a semiconductor memory element such as a random access memory (RAM) and a flash memory, a hard disk, an optical disk, and the like. For example, the memory 141 stores a computer program for circuitry included in the X-ray CT apparatus 10 to perform its functions. Furthermore, the memory 141 stores various information obtained by imaging the subject P. Furthermore, the memory 141 stores a noise reduction processing model generated by the processing circuitry 144 to be described below. Note that the memory 141 may be implemented by a server group (cloud) connected to the X-ray CT apparatus 10 via a network.

The display 142 displays various information. For example, the display 142 displays an image based on a reconstruction process that used projection data acquired in an order determined by the method and system described below. Furthermore, for example, the display 142 displays a graphical user interface (GUI) for receiving various instructions, settings, and the like from a user via the input interface 143. For example, the display 142 is a liquid crystal display or a cathode ray tube (CRT) display. The display 142 may be a desktop type display, or may be composed of a tablet terminal and the like capable of wirelessly communicating with the body of the X-ray CT apparatus 10.

Although the X-ray CT apparatus 10 is described as including the display 142 in FIG. 1, the X-ray CT apparatus 10 may include a projector instead of or in addition to the display 142. Under the control of the processing circuitry 144, the projector can perform projection onto a screen, a wall, a floor, the body surface of the subject P, and the like. As an example, the projector can also perform projection onto any plane, object, space, and the like by projection mapping.

The input interface 143 receives various input operations from a user, converts the received input operations into electrical signals, and outputs the electrical signals to the processing circuitry 144. For example, the input interface 143 is implemented by a mouse, a keyboard, a trackball, a switch, a button, a joystick, a touch pad for performing an input operation by touching an operation surface, a touch screen in which a display screen and a touch pad are integrated, non-contact input circuitry using an optical sensor, voice input circuitry, and the like. Note that the input interface 143 may be composed of a tablet terminal and the like capable of wirelessly communicating with the body of the X-ray CT apparatus 10. Furthermore, the input interface 143 may be circuitry that receives an input operation from a user by motion capture. As an example, the input interface 143 can receive a user's body movement, line of sight, and the like as an input operation by processing a signal acquired via a tracker or an image collected for a user. Furthermore, the input interface 143 is not limited to one including physical operation parts such as a mouse and a keyboard. For example, an example of the input interface 143 includes electric signal processing circuitry which receives an electric signal corresponding to an input operation from an external input device separately provided from the X-ray CT apparatus 10 and outputs the electric signal to the processing circuitry 144.

The processing circuitry 144 controls the overall operation of the X-ray CT apparatus 10 by performing a control function 144a, an imaging function 144b, an acquisition function 144c, and an output function 144f. Depending on the functions to be performed, the processing circuitry also may include at least one of a noise reduction function 144e and a model generation function 144d (e.g., when producing an updated model to address imaging issues).

For example, the processing circuitry 144 reads a computer program corresponding to the control function 144a from the memory 141 and executes the read computer program, thereby controlling various functions, such as the imaging function 144b, the acquisition function 144c, the model generation function 144d, the noise reduction processing function 144e, and the output function 144f, based on various input operations received from a user via the input interface 143.

Furthermore, for example, the processing circuitry 144 reads a computer program corresponding to the imaging function 144b from the memory 141 and executes the read computer program, thereby imaging the subject P. For example, the imaging function 144b controls the X-ray high voltage device 114 to supply the X-ray tube 111 with a high voltage. With this, the X-ray tube 111 generates X-rays to be emitted to the subject P. Furthermore, the imaging function 144b controls the couch driving device 132 to move the subject P into an imaging port of the gantry 110. Furthermore, the imaging function 144b adjusts the position of the wedge 116 and the opening degree and position of the collimator 117, thereby controlling the distribution of the X-rays emitted to the subject P. Furthermore, the imaging function 144b controls the control device 115 to rotate the rotating part. Furthermore, while the imaging is performed by the imaging function 144b, the DAS 118 acquires X-ray signals from the respective detection elements in the X-ray detector 112 and generates detection data.

Furthermore, the imaging function 144b performs preprocessing on the detection data output from the DAS 118. For example, the imaging function 144b performs preprocessing, such as logarithmic transformation processing, offset correction processing, inter-channel sensitivity correction processing, and beam hardening correction, on the detection data output from the DAS 118. Note that the data subjected to the pre-processing is also described as raw data. Furthermore, the detection data before the pre-processing and the raw data subjected to the pre-processing are also collectively described as projection data.

Furthermore, for example, the processing circuitry 144 reads a computer program corresponding to the acquisition function 144c from the memory 141 and executes the read computer program, thereby acquiring noise data and/or training data to help model the noise conditions of the CT system. Furthermore, for example, the processing circuitry 144 reads a computer program corresponding to the model generation function 144d from the memory 141 and executes the read computer program, thereby generating a model of the CT system having the acquired noise data and/or training data. Furthermore, for example, the processing circuitry 144 reads a computer program corresponding to the noise reduction processing function 144e from the memory 141 and executes the read computer program, thereby reducing noise in input subject data and obtaining denoised data. Furthermore, for example, the processing circuitry 144 reads a computer program corresponding to the output function 144f from the memory 141 and executes the read computer program, thereby outputting an image based on the order of acquisition of the projection data. The image may first have been denoised.

In the X-ray CT apparatus 10 illustrated in FIG. 1, the respective processing functions are stored in the memory 141 in the form of the computer programs executable by a computer. The processing circuitry 144 is a processor that performs a function corresponding to each computer program by reading and executing the computer program from the memory 141. In other words, the processing circuitry 144 having read the computer program has a function corresponding to the read computer program.

Note that, in FIG. 1, it has been described that the control function 144a, the imaging function 144b, the acquisition function 144c, the model generation function 144d, the noise reduction processing function 144e, and the output function 144f are implemented by the single processing circuitry 144, but the processing circuitry 144 may be configured by combining a plurality of independent processors, and each processor may be configured to perform each function by executing each computer program. Furthermore, each processing function of the processing circuitry 144 may be performed by being appropriately distributed or integrated into a single circuit (e.g., a field programmable gate array (FPGA)) or a plurality of processing circuits.

Furthermore, the processing circuitry 144 may also perform the functions by using a processor of an external device connected via the network. For example, the processing circuitry 144 reads and executes the computer program corresponding to each function from the memory 141 and uses, as computation resources, a server group (cloud) connected to the X-ray CT apparatus 10 via the network, thereby performing each function illustrated in FIG. 1.

Furthermore, although FIG. 1 illustrates only the single memory 141, the X-ray CT apparatus 10 may include a plurality of physically separated memories. For example, the X-ray CT apparatus 10 may separately include, as the memory 141, a memory that stores a computer program required when circuitry included in the X-ray CT apparatus 10 performs its function, a memory that stores various information obtained by imaging the subject P, and a memory that stores the noise reduction processing model.

Using at least one image acquisition apparatus/system, an order of acquisition of projections can be determined for at least one imaging task to be performed. As part of such a determination, a simulator system (sometimes referred to simply as a simulator) is generated, using processing circuitry as described here, that generates simulated 3D volume data under a set of simulated imaging conditions by extracting projection data from acquired CT volume image data (e.g., by using forward projection). For example, as part of a method 200 of FIG. 2, a set of view parameters (e.g., a number of views to be taken and the angles at which the views should be taken) and imaging parameters (e.g., radiation dosage(s)) can be used to cause a CT device to acquire a series of projections. In light of the use of a phantom, the radiation dosage can be higher than would typically be used with a living subject, and the number of projections may be significantly larger than would be used to image a living subject. As a result, the obtained projections will generally have a better signal-to-noise ratio than projections that result from imaging a living subject. The acquired projection data can then be used in a reconstruction process (e.g., an iterative reconstruction process or a filtered backpropagation reconstruction process) to produce acquired CT volume image data representing the phantom under the imaging conditions used. In light of the desire to start with the best signal-to-noise ration in the acquired CT volume data, a higher quality reconstruction process (e.g., an iterative reconstruction process) is preferably used. In addition, in producing the acquire CT volume image data, further processing include processing for denoising, reduction of blurring and reduction of scatter can be performed in the projection domain or the image domain.

Figure 2:
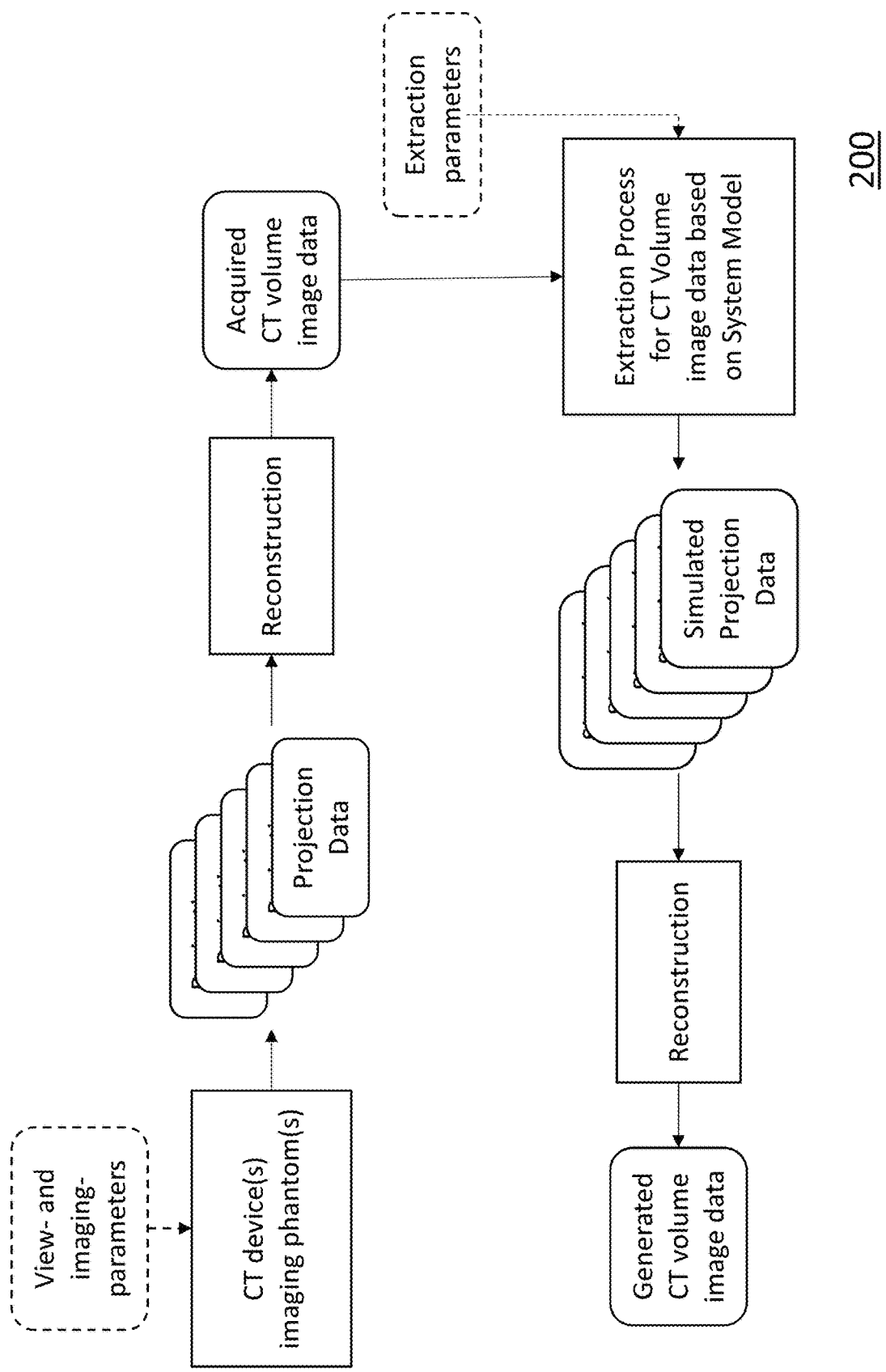
FIG. 2 is an illustrative flow diagram of a generalized process of obtaining projection data by imaging at least one phantom, generating acquired CT volume image data by performing reconstruction on the projection data obtained by imaging the at least one phantom, and generating simulated 3D volume data under a set of simulated imaging conditions (defined by extraction parameters) by (1) extracting simulated projection data from the acquired CT volume image data and (2) performing reconstruction on the simulated projection data.

One the acquired CT volume data is generated, the reverse process can be used to simulate how the same image acquisition apparatus or another image acquisition apparatus would perform a specified imaging task. As shown in FIG. 2, a specified imaging task is converted into a set of imaging parameters which are then converted into extraction parameters that are used to extract projections from the acquired CT volume image data. For example, if an imaging task is selected that requires as imaging parameters fifty (50) views at specified angles and using at least one specified radiation dosage, then those angles and radiation dosages can be used to extract a set of simulated projection data corresponding to the imaging parameters. To simulate the radiation dosages, the system can artificially add a corresponding amount of noise to the projection data as part of the extraction process. The amount of noise to be added can be determined by calculating the amount of noise that exists in phantom images taken at various radiation dosages compared to the radiation dosage used to generate the acquired CT volume image data from which the simulated projections are being extracted.

Once the resulting simulated projection data has been extracted to simulate having performed an imaging task, the simulated projection data can be run through a reconstruction process to produce a corresponding CT volume image data simulating what would have been generated had the imaging task been performed on the phantom at the specified conditions.

Figure 3A:
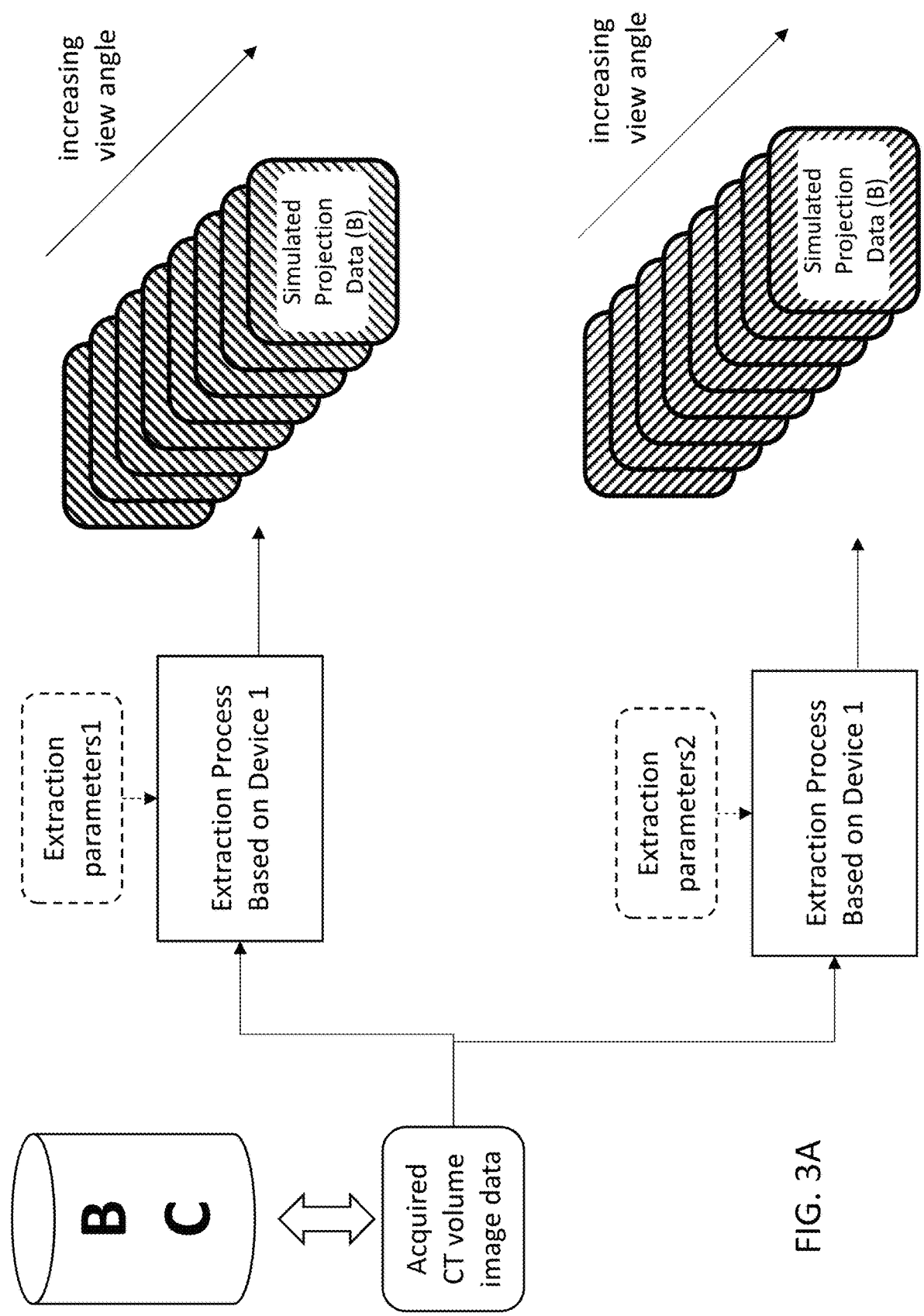
FIGS. 3A-3C are dataflow diagrams illustrating various extraction processes corresponding various imaging devices whereby corresponding series of simulated projection data are extracted from acquired CT volume image data under various extraction parameters to simulate various imaging tasks.
Figure 3B:
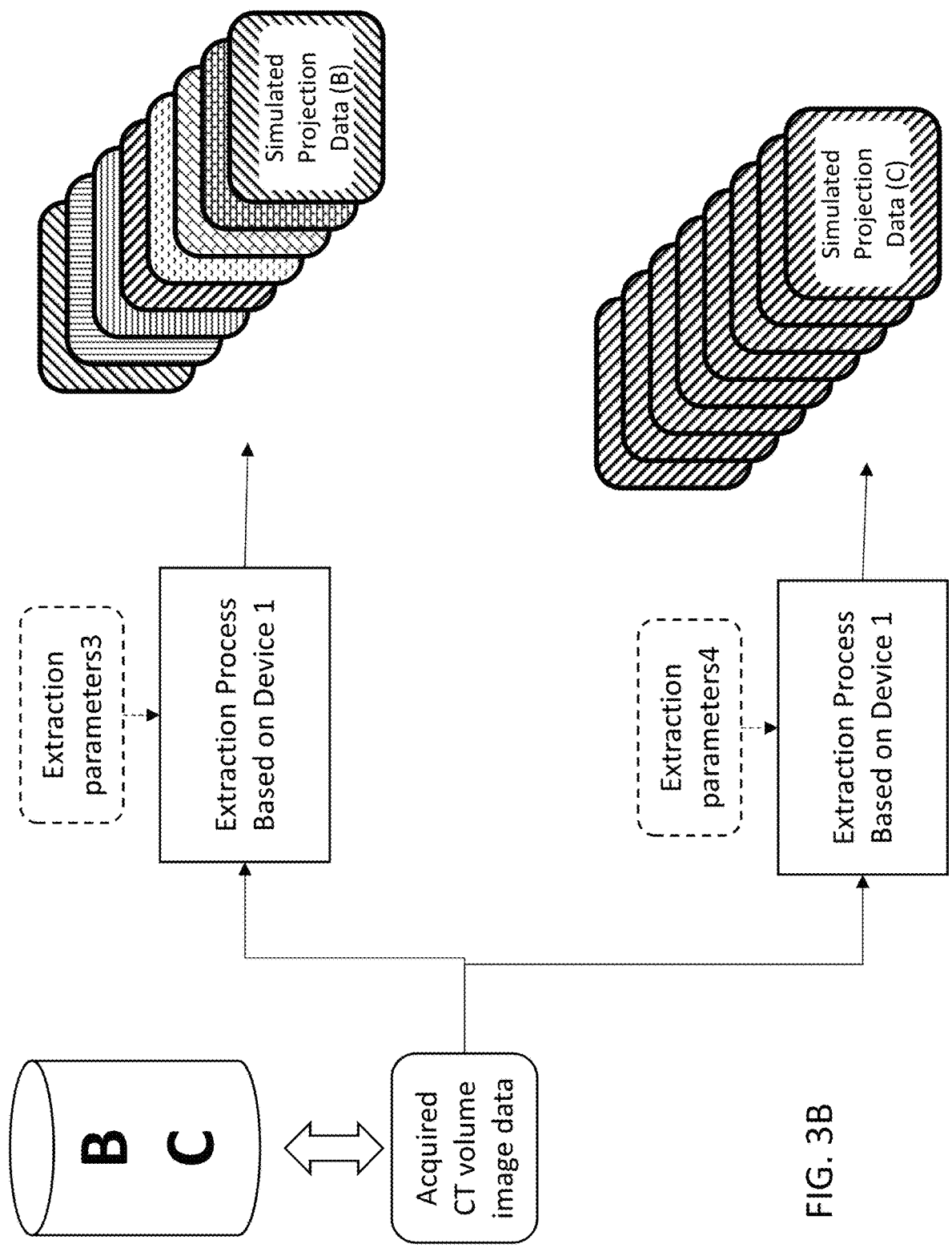
Figure 3C:
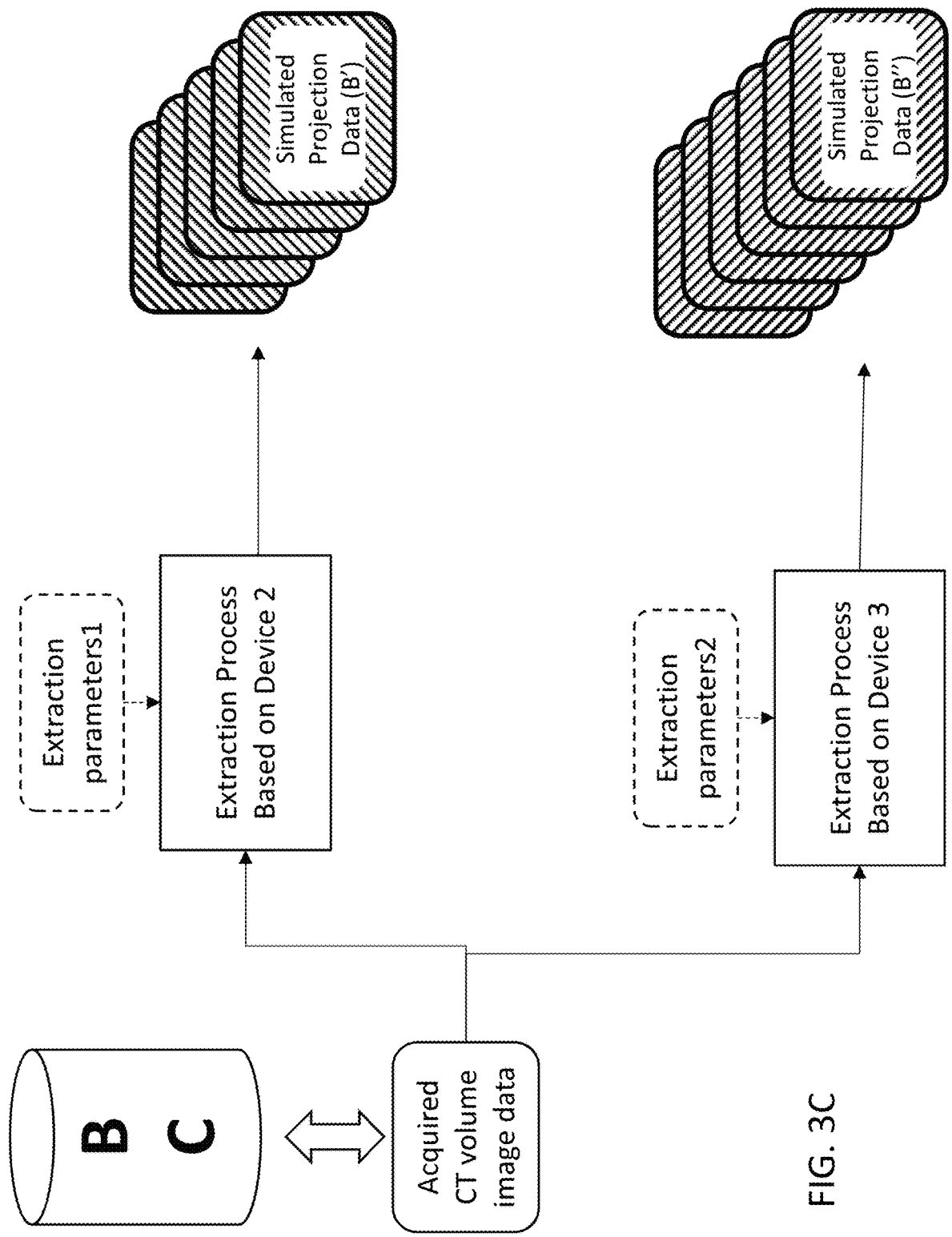

Using the general technique of FIG. 2, it is possible, as shown in FIGS. 3A-3C, to use system models of imaging devices to be simulated to simulate varying imaging tasks. The system models indicate imaging device-specific characteristics that affect how data is extracted from the acquired CT volume image data. As shown in FIG. 3A, acquired CT volume image data is illustrated as having been acquired for a phantom having at least two separate three-dimensional regions (labeled "B" and "C"). By performing an extraction process corresponding to a first device (e.g., Device 1 such as the same CT apparatus that was used to acquire the phantom data), the system produces a first set of simulated projection data (based on increasing or decreasing view angles) for a first three-dimensional region corresponding to region "B" at a particular radiation dosage (and therefore having a particular amount of noise). As would be appreciated, other degradations besides noise (such as blurring and/or scatter) also are possible to be added to the projections as part of the extraction process. As illustrated, a first set of parameters (labeled "parameters1") may utilize a different (constant) radiation dosage than a second set of parameters (labeled "parameters2") while all the other parameters stay the same. As a result, the corresponding dosage associated with each projection may be different (as indicated by the different hatching in the simulated projection data), but, for example, the number of resulting projections stays the same.

As shown in FIG. 3B, a third set of projection parameters (labeled "paramters3") can be used to simulate the same imaging task on the same imaging apparatus (e.g., Device 1) but with varying dosages as might be used with an automatic exposure correction system or as might be used to accommodate for varying radiation levels due to organ sensitivity (e.g., reduced radiation in the presence of breast tissue and increased radiation in the presence of bone or when passing through a table on which the subject rests). As also shown in FIG. 3B, a fourth set of projection parameters (labeled "paramters4") can be used to simulate an imaging task on a different area within the acquired CT volume image data (e.g., the region corresponding to area "C").

By contrast, as shown in FIG. 3C, when a set of extraction parameters that generated one set of projections corresponding to Device 1 are instead applied with respect to Device 2, a different set of projections (e.g., a different number or a different set of angles and/or dosages) can be produced. As shown in FIG. 3C, when the parameters of parameters1 are used to extract projections, a same radiation dosage may be produced but a different number of projections (e.g., because Device 2 has a more limited set of angles that can be produced as compared with Device 1). The same effect is shown in FIG. 3C for yet a third device. This change in the resulting projections can be used to simulate performing an imaging task on devices such as C-arm CT systems and/or tomosynthesis systems even when the original acquired CT volume image data was acquired using a traditional CT system. Although not shown, the extraction parameters for the same imaging task may not be the same on all devices, for example, where two imaging devices do not have the same maximum possible radiation ranges or where they have obstructions that are different such that changes in radiation levels during the imaging tasks vary differently.

Figure 3D:
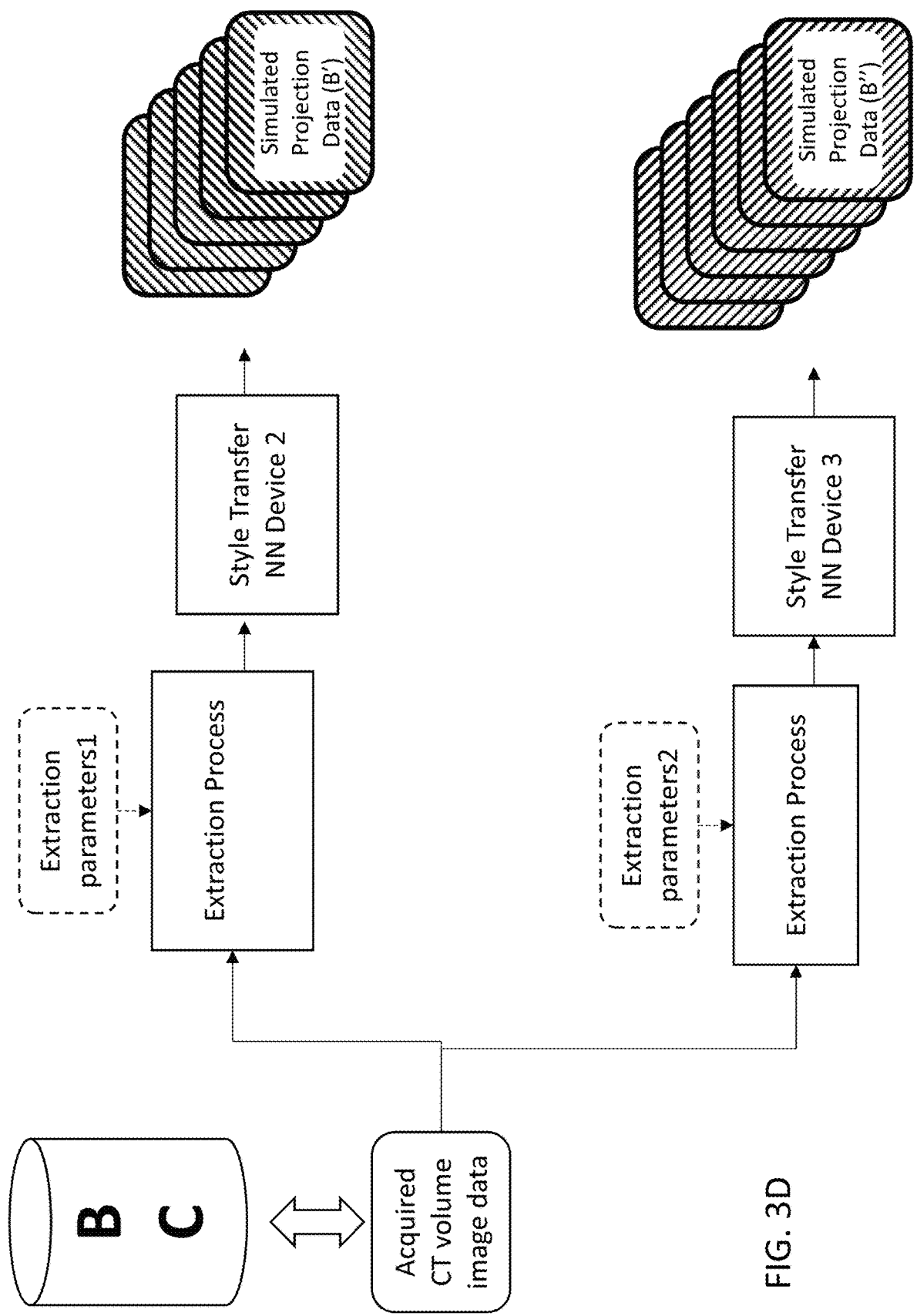
FIG. 3D is a dataflow diagram illustrating various extraction processes corresponding various imaging devices whereby corresponding series of simulated projection data are extracted from acquired CT volume image data under various extraction parameters and applied to style transfer neural networks to simulate various imaging tasks on various devices.

Alternatively, instead of using the system models used in FIGS. 3A-3C, a system and/or method alternatively can use at least one style transfer neural network as shown in FIG. 3D to simulate the effects of acquiring the data of the acquired CT volume image data on at least one imaging device other than the imaging device on which the acquired CT volume image data was acquired.

Figure 4A:
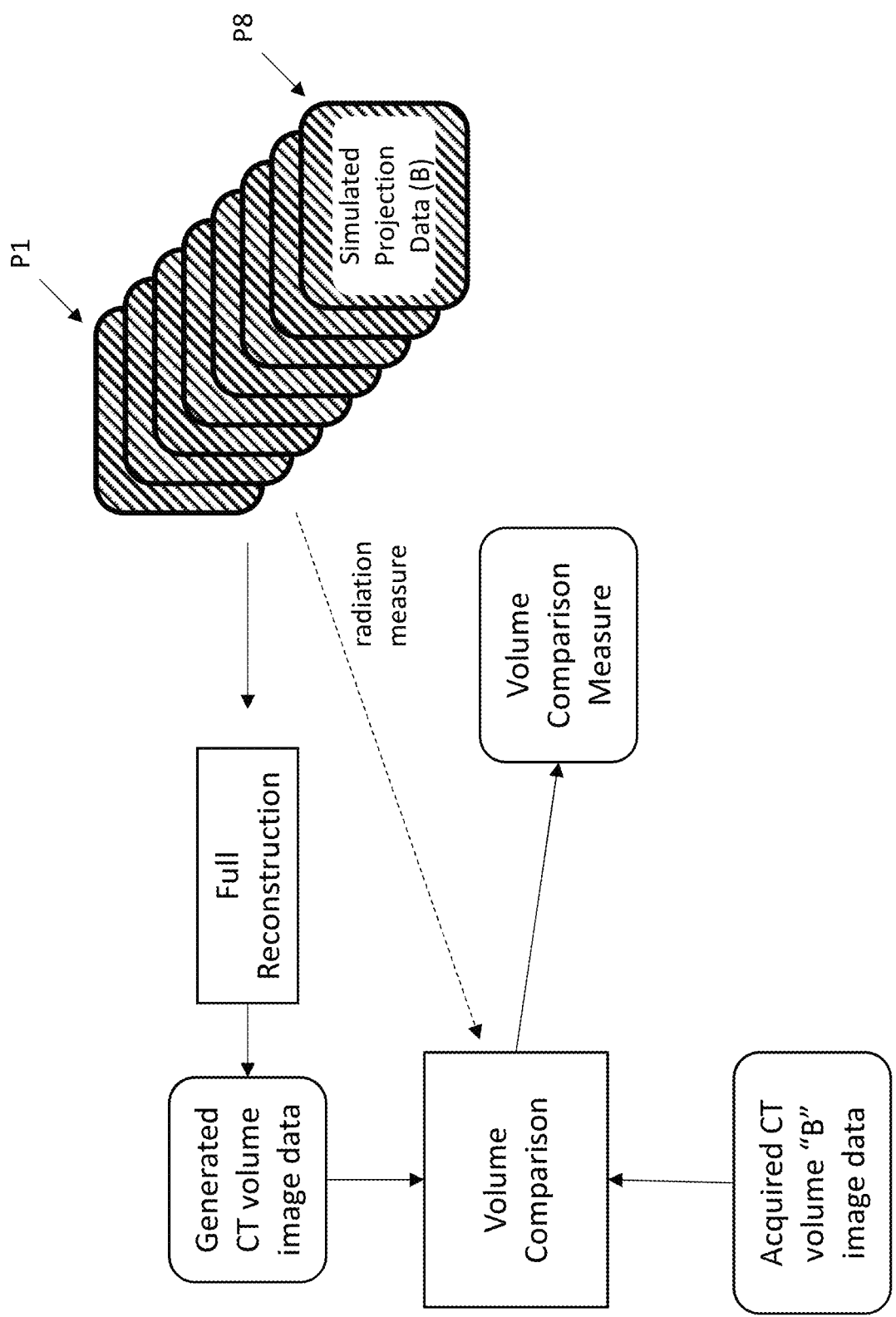
FIG. 4A is a dataflow diagram illustrating how a full reconstruction process can be performed on simulated projection data and compared against a corresponding part of the acquired CT volume image data used to generate the simulated projection data to assess how well the generated CT volume image data represents the corresponding part of the acquired CT volume image data.
Figure 4B:
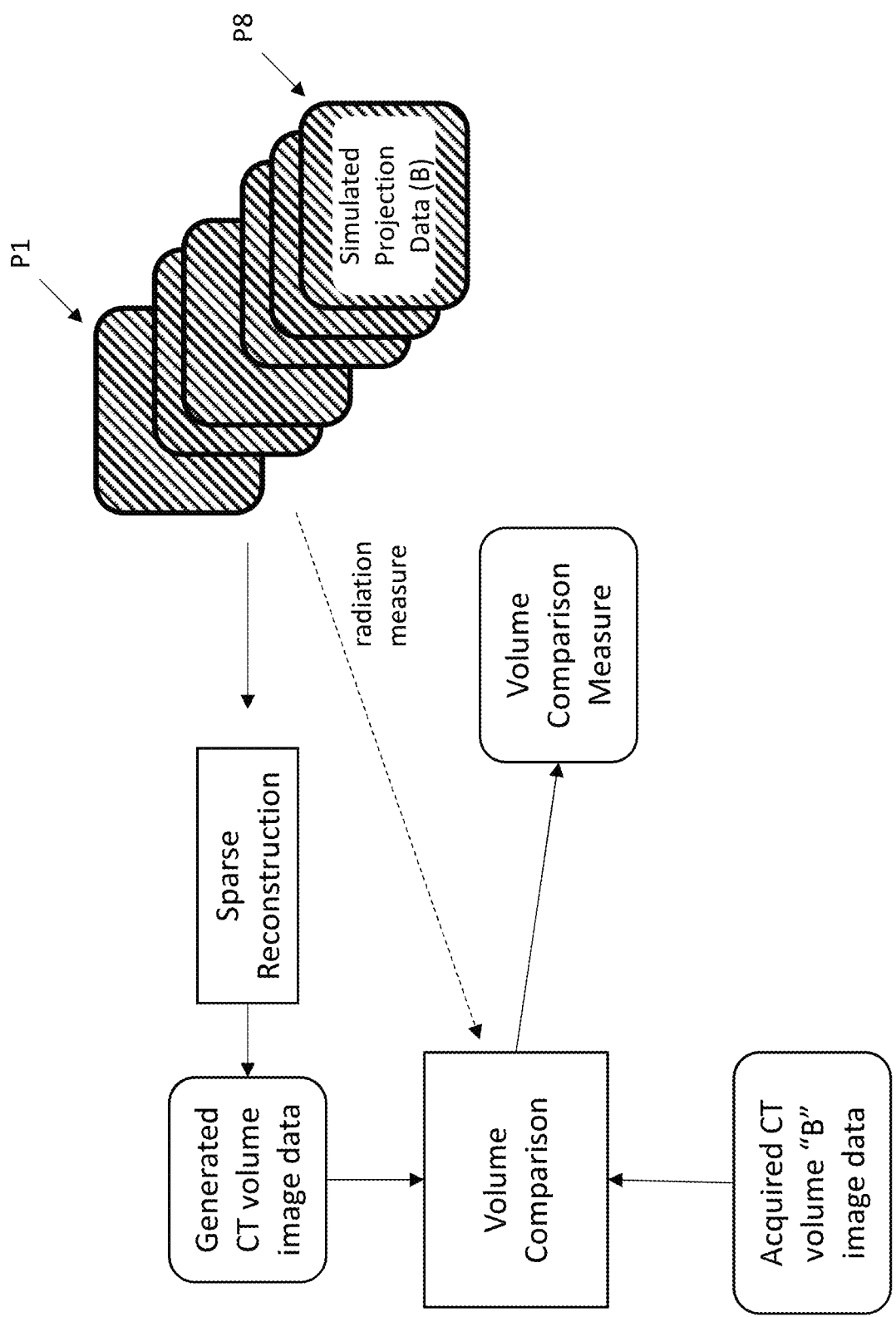
FIG. 4B is a dataflow diagram illustrating how a sparse reconstruction process can be performed on simulated sparse projection data and compared against a corresponding part of the acquired CT volume image data used to generate the simulated sparse projection data to assess how well the generated CT volume image data represents the corresponding part of the acquired CT volume image data.
Figure 4C:
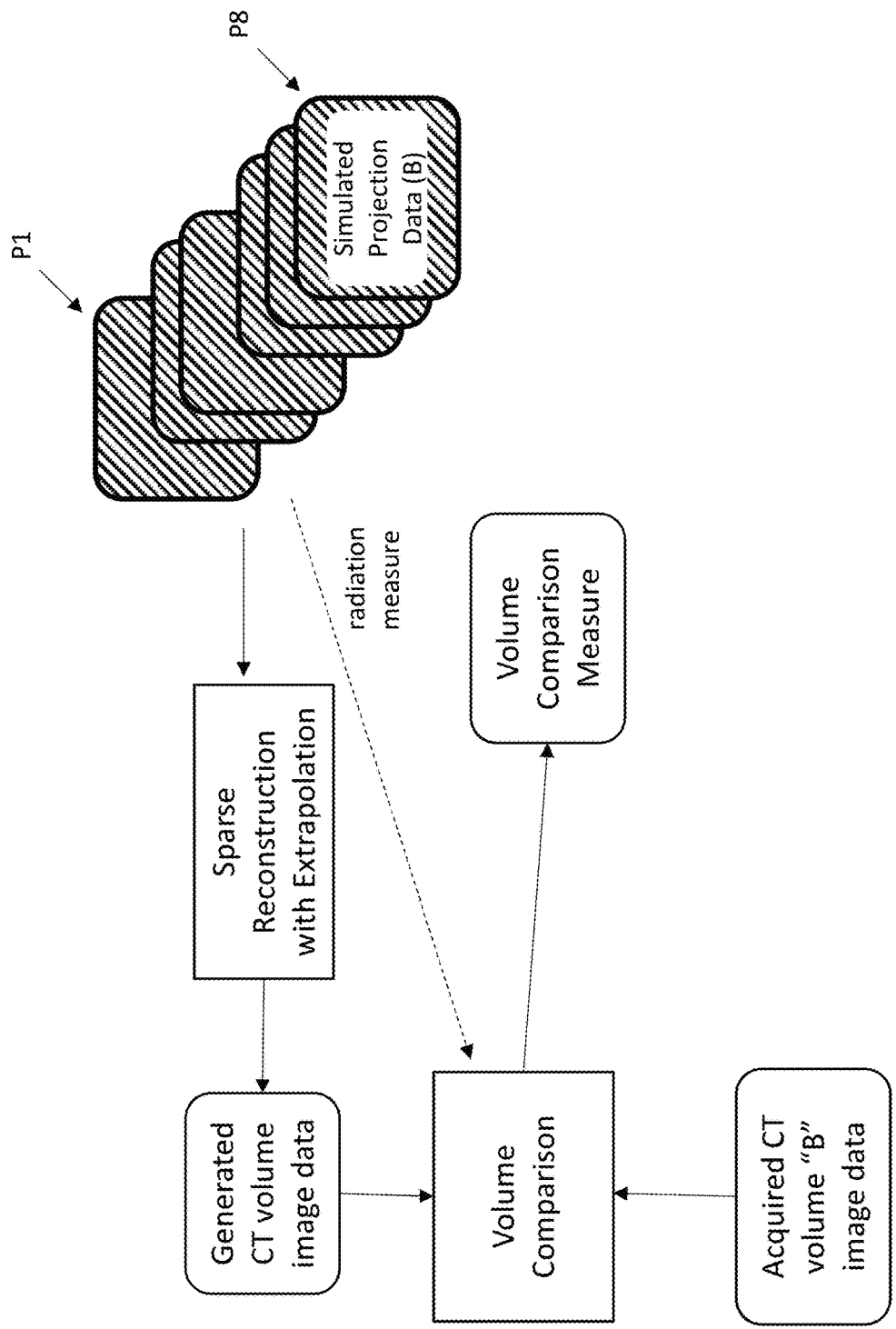
FIG. 4C is a dataflow diagram illustrating how a sparse reconstruction process with extrapolation can be performed on simulated sparse projection data and compared against a corresponding part of the acquired CT volume image data used to generate the simulated sparse projection data to assess how well the generated CT volume image data represents the corresponding part of the acquired CT volume image data.

Given the creation of a simulator, a system can learn to optimize various imaging protocols for an imaging task to be performed. For example, as shown in FIG. 4A, an original imaging task is converted into a preliminary set of eight projections (corresponding to a preliminary set of 8 (constant) dosages) that could be applied to a full reconstruction process to produce a first set of generated CT volume image data at a cost of the sum of the radiations used for each of the projections. However, as shown in FIG. 4B, a sparse reconstruction process can be used instead which allows fewer projections to be taken and lowers the amount of radiation administered during imaging. The sparse reconstruction process utilizes interpolation between projections to "fill in" data that was not acquired because of the reduction in the number of projections. As shown in FIG. 4C, in addition to performing data interpolation between projections, it also is possible to perform sparse reconstruction with extrapolation to effectively add data to beyond the ends of where projections were obtained, either because the imaging device being simulated has a more limited set of angles (e.g., in C-arm CT systems and/or tomosynthesis systems) or because projections were selected that did not extend to the fullest extent of the range over which the device was capable of imaging. As should be appreciated, the system can run both a sparse reconstruction and a sparse reconstruction with extrapolation in parallel and learn which of the two reconstructions performs better for a particular imaging task. In addition, other reconstruction processes can be run in parallel as well to determine which reconstruction process best reconstructs a particular set of projections.

By varying the projections to be used and measuring the image quality (as compared with a corresponding portion of the original acquired CT volume image data which is labeled as acquired CT volume "B" image data), the system can be programmed to learn a set of projection parameters that is optimized to achieve a particular imaging objective. For example, a volume comparison measure can be generated as part of a volume comparison function such that the system can utilize a weighted combination of factors that represent the imaging objective. For example, a weighted combination of (1) an image quality parameter (measuring how close the generated CT volume image data is to the acquired CT volume image data) and (2) a radiation dosage can be used. Other parameters (e.g., overall time) can be considered as well and included in the weighted combination. How the weighted parameters are weighted itself may be part of the imaging task information. For example, if the patient to be imaged is radiation sensitive, the weighting factors may be set to prioritize lower radiation dosage at the risk of lower image quality as compared to the weighting factors that are used for a patient that is not radiation sensitive. Moreover, an imaging task may be used that is designed to prioritize image quality over radiation dosage or that seeks to have the best image quality while not exceeding a particular radiation threshold (which again may vary based on other parameters). Generally, the factors of the weighted combination are at odds with each other. For example, by increasing a number of projections used in the reconstruction process, an image quality may improve. However, increasing the number of projections also in some circumstances increases an amount of radiation during the imaging process.

Once the imaging task parameters are established, however, the system selects variations in the corresponding projections to attempt to learn an optimized set of projections that achieves the goal of the imaging task. The system can be programmed to learn the projections to be used using either short-term objectives or long-term objectives.

In one embodiment, the system utilizes a deep reinforcement learning neural network that starts with a particular projection that is either always fixed (e.g., from a particular angle) or that is selected by a medical professional. Having selected which projection to begin with at a particular dosage, the network uses, as a greedy reward function, a weighted combination of image quality and radiation dosage such that the network learns the effect of adding each of the possible projections. For example, the network can learn what the value of the greedy reward function is when a projection is used with other projections extracted by the neural network. Having found that, for example, at a first dosage a first projection provides the highest reward value in combination with another projection, the network then attempts to find a next projection that again optimizes the greedy reward function. Thus, a local neural network is able to determine an optimized set of projections to use to satisfy an imaging task.

One example of the reward function at a step n is
MSE(output[n], CT)−MSE(output[n−1], CT)−dose term, where MSE is the mean-squared error; Output[n] is the output volume at step n; and Output[n−1] is the output volume at step n−1

Although the above has been described with respect to learning an optimized set of projections using a neural network, it is possible to apply an iterative approach or a recursive approach to the selection and testing of various combinations of projections. Moreover, an iterative approach can optionally use a series of different dosages close to (above and below) an estimated dosage for each possible projection angle and thereby vary dosage and angle when searching for a set of projections to optimize an imaging task.

Having determined an optimized set of projections (and dosages) for a particular imaging task, the optimized set of projections (and dosages) are programmed into an imaging apparatus of the kind modeled during the training process so that the imaging apparatus can perform optimized imaging for the corresponding imaging task. As would be appreciated by those of skill in the art, the optimization procedures described herein can be performed prior to imaging procedures to be optimized by the above-methods or dynamically such that they are performed dynamically in conjunction with the imaging procedures which are being optimized.

Figure 6:
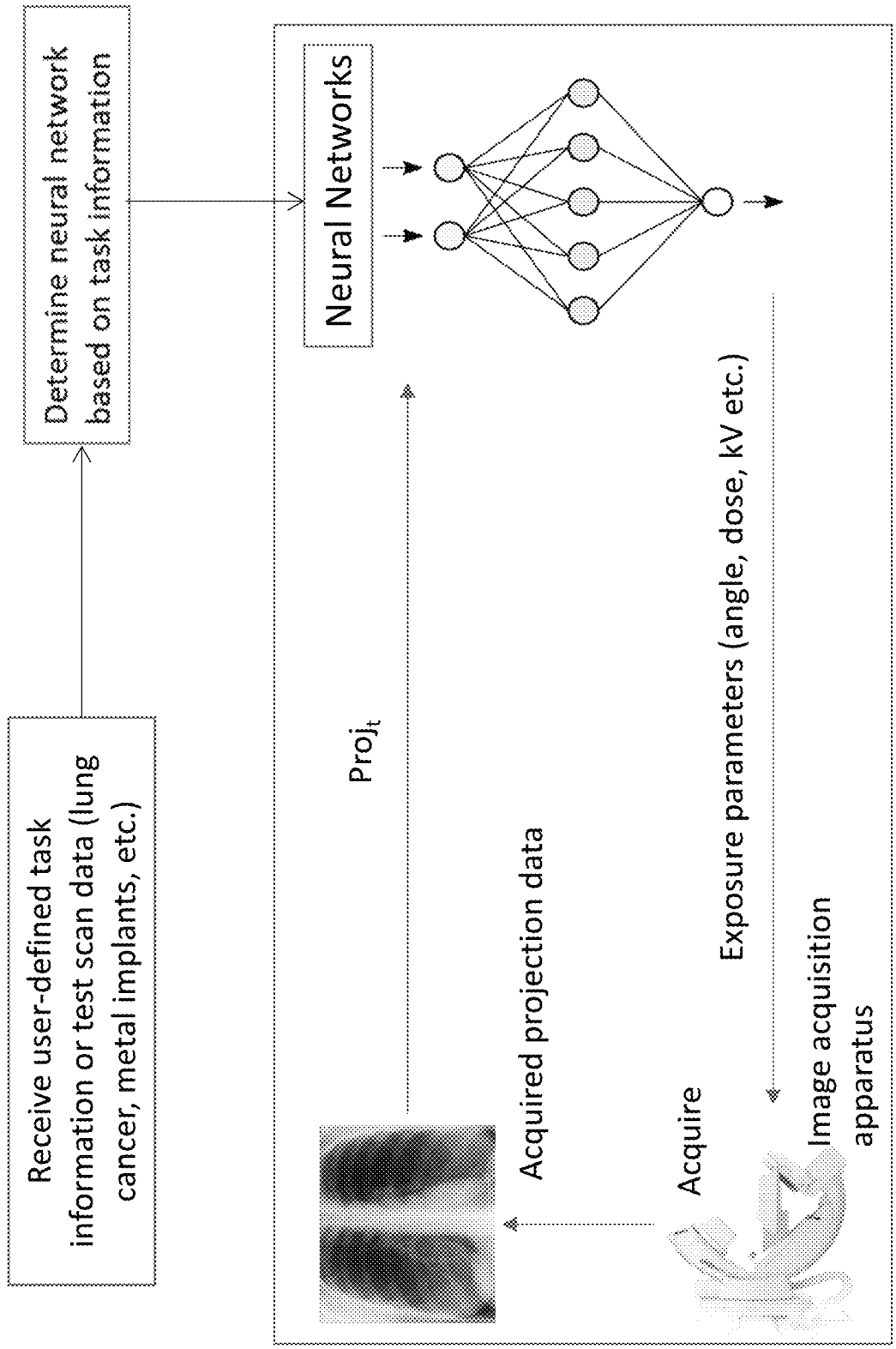
FIG. 6 is a flowchart of the use of the one or more trained neural networks of FIG. 5 in the automatic, dynamic, and task-aware sparse-view acquisition planning method, in one embodiment.
Figure 7:
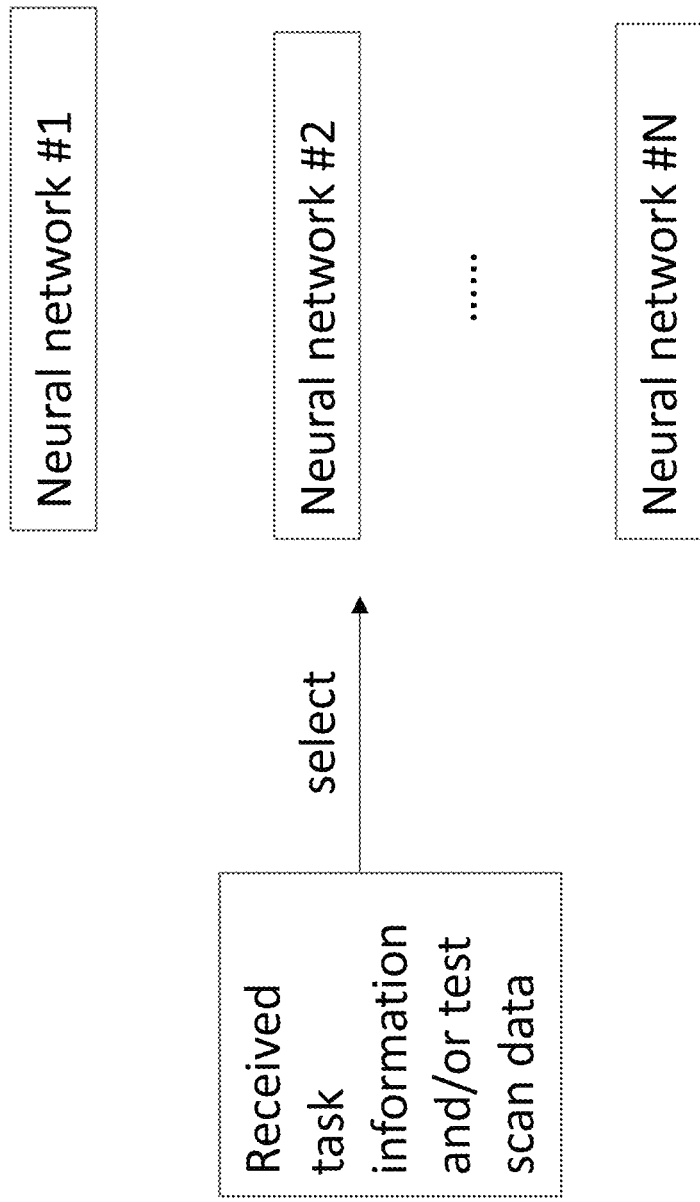
FIG. 7 illustrates a process of selecting a neural network based on a defined task or test scan information.

In another embodiment, FIG. 6 illustrates an automatic, dynamic, and task-aware sparse-view acquisition planning method based on a greedy strategy. In the method of this embodiment, user-defined task information (e.g., a body part to be imaged, the purpose of the imaging, lung cancer information, and/or metal-implant information) and/or test scan information is provided to determine or select from among one or more pre-trained neural network having been trained for use with such task information. As shown in FIG. 7, the particular task information and/or test scan information is used to select/determine an appropriate trained neural network, e.g. using a predetermined table (or other data structure) associating different types of task information and/or test scan data with different trained networks or network identifiers. The selected neural network, which is trained using the method shown in FIG. 6 (discussed in more detail below) receives acquired projection data $Proj_t$ as input and produces, as output, imaging conditions, such as exposure parameters (angle, dose, kV, etc.) to be used by the image acquisition apparatus (e.g., a computed tomography (CT) system, a C-arm CT system, and a tomosynthesis system) to dynamically control the next acquisition. The imaging conditions can also include a condition of view interpolation and/or a condition of view extrapolation. New projection data is then obtained by the image acquisition apparatus in the next acquisition using the exposure parameters output from the neural network.

Figure 5:
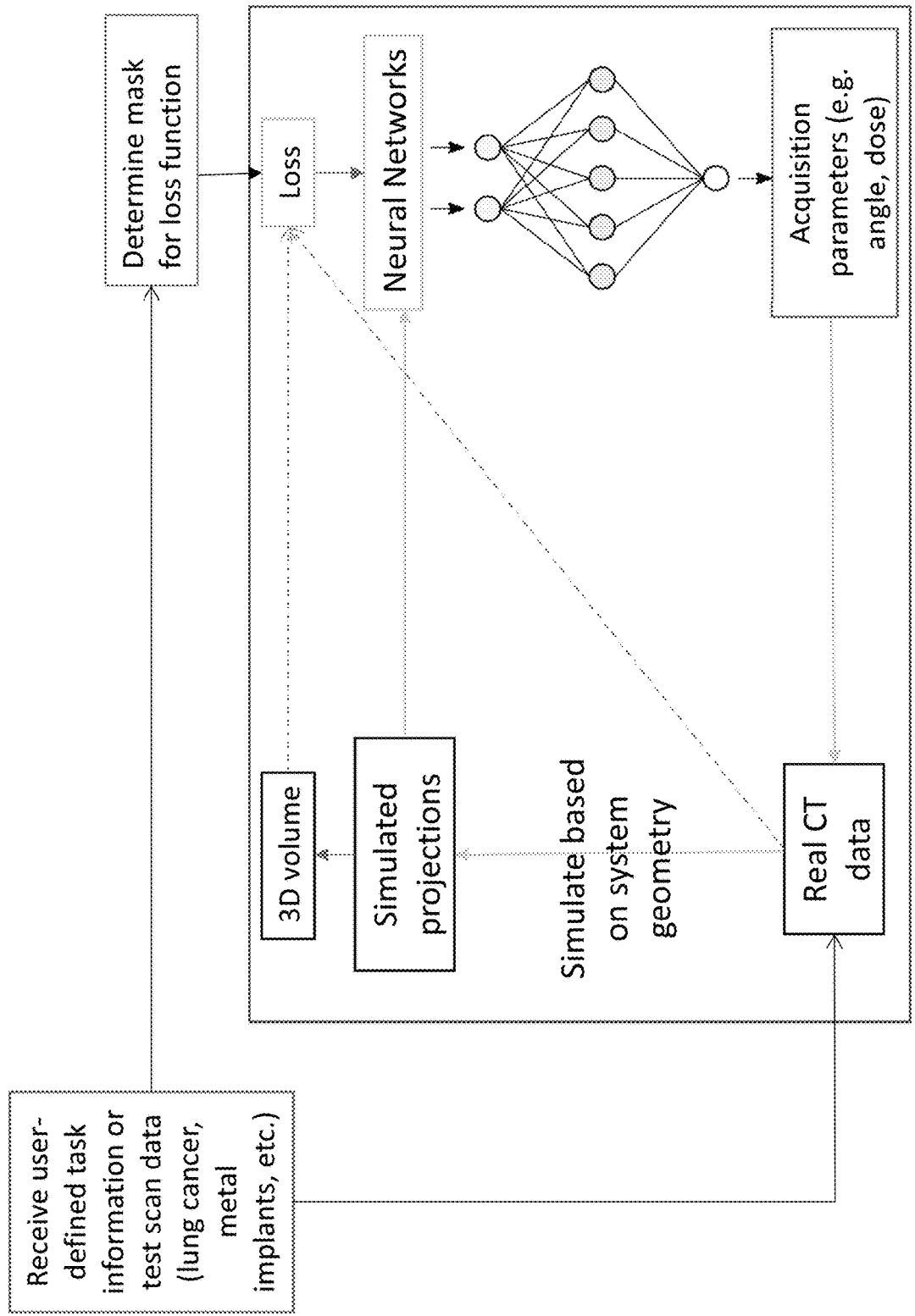
FIG. 5 is a flowchart of a method of training one or more neural networks according for use in an automatic, dynamic, and task-aware sparse-view acquisition planning method using a greedy reward function, in one embodiment.

As shown in FIG. 5, each neural network is trained with a training method based on deep reinforcement learning with a greedy reward function. The reward function is calculated after obtaining each projection image, and is composed of two parts, in one example. First, the reward function includes an image quality term obtained by comparing the ground truth volume data (corresponding to the user-defined task information or test scan data) and the 3D volume data obtained from reconstruction of the simulated projections after each step. As shown in FIG. 5, the user-defined task information is also used in determining the image quality term, e.g., a mask can be applied to the regions of interest based on the user-defined task information. Second, as noted above, the reward function can include a dose constraint to limit dosage. Further, as shown in FIG. 5, the reward function is used to modify/update the neural network, which outputs the acquisition parameters used to determine the simulated projections.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

Embodiments of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of data processing apparatus. Alternatively, or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), or a portable storage device, e.g., a universal serial bus (USB) flash drive, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CDROM and DVD-ROM disks. The processor and the memory can be Supplemented by, or incorporated in, special purpose logic circuitry.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more Such back-end, middleware, or frontend components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the user device, which acts as a client. Data generated at the user device, e.g., a result of the user interaction, can be received from the user device at the server.

While this specification contains many specific implementation details, these should not be construed as limitations on the scope of what may be claimed, but rather as descriptions of features that may be specific to particular embodiments.

Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

Numerous modifications and variations are possible in light of the above teachings. It is therefore to be understood that within the scope of the appended claims, the invention may be practiced otherwise than as specifically described herein.

Embodiments of the present disclosure may also be as set forth in the following parentheticals.

(1) A method for performing image acquisition control, including, but not limited to: (a) acquiring CT volume image data; (b) extracting from the CT volume image data a plurality of simulated projections used to simulate a plurality of projection acquisitions under a set of imaging conditions simulating projection acquisitions using an image acquisition apparatus; and (c) determining a sparse subset of the plurality of simulated projections that, when reconstructed by a sparse reconstruction process, produces generated image volume data corresponding to an optimized image quality and an optimized radiation dosage.

(2) The method according to (1), wherein determining the sparse subset of the plurality of simulated projections includes, but is not limited to, determining the sparse subset of the plurality of simulated projections by training a first untrained machine learning system to satisfy at least one of maximizing a reward function and minimizing a loss function.

(3) The method according to (2), wherein the first untrained machine learning system is a deep reinforcement learning neural network.

(4) The method according to (2), wherein determining the sparse subset of the plurality of simulated projections by training the first untrained machine learning system to satisfy at least one of maximizing a reward function and minimizing a loss function includes, but is not limited to, training the first untrained machine learning system to satisfy a greedy reward function.

(5) The method according to any one of (1)-(4), wherein the set of imaging conditions simulating projection acquisitions using the image acquisition apparatus comprise a set of imaging angles and radiation dosages.

(6) The method according to (5), wherein extracting from the CT volume image data the plurality of simulated projections used to simulate the plurality of projection acquisitions under the set of imaging conditions simulating projection acquisitions using the image acquisition apparatus includes, but is not limited to, simulating the radiation dosage by adding at least one of blurring, noise, and scatter to the plurality of simulated projections during extraction.

(7) The method according to (6), wherein adding the at least one of blurring, noise, and scatter to the plurality of simulated projections during extraction includes, but is not limited to, adding the at least one of blurring, noise, and scatter to the plurality of simulated projections during extraction using a model of the image acquisition apparatus.

(8) The method according to (6), wherein adding the at least one of blurring, noise, and scatter to the plurality of simulated projections during extraction includes, but is not limited to, adding the at least one of blurring, noise, and scatter to the plurality of simulated projections during extraction using a style transfer neural network corresponding to the image acquisition apparatus.

(9) The method according to any one of (1)-(8), further including, but not limited to: acquiring a simulated test scan including plural test scan projections simulated to each have been taken at a respective angle and a respective dose; selecting as an initial scan angle and an initial scan dosage the respective angle and the respective dose of a test scan projection of the plural test scan projections that optimizes a result of repeatedly applying the first loss function.

(10) The method according to (9), wherein optimization of the result of repeatedly applying the first loss function comprises optimizing a long-term global reward function based on plural sets of 3D volume image data.

(11) The method according to any one of (1)-(10), wherein the image acquisition apparatus includes, but is not limited to, at least one of a computed tomography (CT) system, a C-arm CT system, and a tomosynthesis system.

(12) The method according to (11), wherein the image acquisition apparatus comprises at least one of a C-arm CT system and a tomosynthesis system, and wherein the sparse reconstruction process is an extrapolating reconstruction process that supplements the plurality of simulated projections with additional simulated projections corresponding to projection angles that cannot be acquired using the image acquisition apparatus.

(13) An imaging apparatus including, but not limited to, processing circuitry configured to perform the methods of any one of (1)-(12).

(14) method for determining a set of imaging conditions for an image acquisition apparatus, the method comprising: obtaining a trained neural network, the trained neural network having projection data as inputs and the set of imaging conditions as outputs, and being trained based on particular task information and/or test scan data; applying first projection data to the trained neural network to obtain a first set of imaging conditions; and obtaining the first set of imaging conditions as outputs from the trained neural network, wherein the imaging conditions include at least one of a condition of view interpolation and a condition of view extrapolation.

(15) The method of (14), further comprising determining a second set of imaging conditions by dynamically adjusting the first set of imaging conditions, according to an image acquired based on the obtained first set of imaging conditions; and controlling the image acquisition apparatus, based on the determined second set of imaging conditions, to perform a scan to obtain second projection data.

(16) The method of (14), wherein the image acquisition apparatus comprises at least one of a computed tomography (CT) system, a C-arm CT system, and a tomosynthesis system.

(17) The method of (14), further comprising training the neural network via a training process with a greedy reward function, which includes an image quality term and a dose-constraint term, wherein the image quality term, at each iteration of the training process, includes a difference between ground truth volume data, determined from the particular task information and/or the test scan data, and particular volume data obtained at the iteration of the training process.

(18) The method of (17), further comprising generating the particular volume data at each iteration of the training process via reconstruction of simulated projections, which are obtained from the ground truth volume data and based on system geometry.

(19) The method of (14), wherein the first set of imaging conditions include exposure parameters, which are at least one of an angle, a dose, or an energy value.

(20) The method of (17), wherein the neural network is trained via the training process, which includes applying a mask to regions of interest based on the particular task information and/or the test scan data.

(21) The method of (14), further comprising: receiving the particular task information and/or the test scan data, and storing, in a memory, a data structure associating, for each network identifier of a plurality of neural network identifiers, a corresponding set of task information and/or test scan data, wherein the obtaining step further comprises determining a particular network identifier identifying the trained neural network, based on the stored data structure and the received particular task information and/or the test scan data.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for performing image acquisition control, comprising:
   acquiring CT volume image data;
   extracting, from the CT volume image data, a plurality of simulated projections used to simulate a plurality of projection acquisitions under a set of imaging conditions simulating projection acquisitions using an image acquisition apparatus; and
   determining a sparse subset of the plurality of simulated projections that, when reconstructed by a sparse reconstruction process, produces generated image volume data corresponding to an optimized image quality and an optimized radiation dosage,
   wherein the determining step further comprises determining the sparse subset of the plurality of simulated projections by using a machine learning system.

2. The method according to claim 1, wherein the determining step further comprises determining the sparse subset of the plurality of simulated projections by training a first untrained machine learning system to satisfy at least one of maximizing a reward function and minimizing a loss function.

3. The method according to claim 2, wherein the first untrained machine learning system is a deep reinforcement learning neural network.

4. The method according to claim 2, wherein the determining step further comprises training the first untrained machine learning system to satisfy a greedy reward function.

5. The method according to claim 1, wherein the set of imaging conditions simulating the projection acquisitions using the image acquisition apparatus comprise a set of imaging angles and radiation dosages.

6. The method according to claim 5, wherein the extracting step further comprises simulating the radiation dosage by adding at least one of blurring, noise, and scatter to the plurality of simulated projections during extraction.

7. The method according to claim 6, wherein the step of adding the at least one of blurring, noise, and scatter to the plurality of simulated projections during extraction further comprises adding the at least one of blurring, noise, and scatter to the plurality of simulated projections during extraction using a model of the image acquisition apparatus.

8. The method according to claim 6, wherein the step of adding the at least one of blurring, noise, and scatter to the plurality of simulated projections during extraction further comprises adding the at least one of blurring, noise, and scatter to the plurality of simulated projections during extraction using a style transfer neural network corresponding to the image acquisition apparatus.

9. The method according to claim 1, further comprising:
   acquiring a simulated test scan including plural test scan projections simulated for each of a respective angle and a respective dose; and
   selecting, as an initial scan angle and an initial scan dosage, the respective angle and the respective dose of a test scan projection of the plural test scan projections that optimizes a result of repeatedly applying a first loss function.

10. The method according to claim 9, wherein the optimization of the result of repeatedly applying the first loss function further comprises optimizing a long-term global reward function based on plural sets of 3D volume image data.

11. The method according to claim 1, wherein the image acquisition apparatus comprises at least one of a computed tomography (CT) system, a C-arm CT system, and a tomosynthesis system.

12. The method according to claim 11, wherein the image acquisition apparatus comprises at least one of a C-arm CT system and a tomosynthesis system, and
   wherein the sparse reconstruction process is an extrapolating reconstruction process that supplements the plurality of simulated projections with additional simulated projections corresponding to projection angles that cannot be acquired using the image acquisition apparatus.

13. An imaging apparatus, comprising:
   processing circuitry configured to
      acquire CT volume image data;
      extract, from the CT volume image data, a plurality of simulated projections used to simulate a plurality of projection acquisitions under a set of imaging conditions simulating projection acquisitions using an image acquisition apparatus; and
      determine a sparse subset of the plurality of simulated projections that, when reconstructed by a sparse reconstruction process, produces generated image volume data corresponding to an optimized image quality and an optimized radiation dosage,
   wherein the processing circuitry is further configured to determine the sparse subset of the plurality of simulated projections by using a machine learning system.

14. A method for determining a set of imaging conditions for an image acquisition apparatus, the method comprising:
   obtaining a trained neural network, the trained neural network having projection data as inputs and the set of imaging conditions as outputs, and being trained based on particular task information and/or test scan data;
   applying first projection data to the trained neural network to obtain a first set of imaging conditions; and
   obtaining the first set of imaging conditions as outputs from the trained neural network,
   wherein the imaging conditions include at least one of a condition of view interpolation for supplementing projection data in image reconstruction and a condition of view extrapolation for supplementing the projection data in the image reconstruction.

15. The method of claim 14, further comprising:
  determining a second set of imaging conditions by dynamically adjusting the first set of imaging conditions, according to an image acquired based on the obtained first set of imaging conditions; and
  controlling the image acquisition apparatus, based on the determined second set of imaging conditions, to perform a scan to obtain second projection data.

16. The method of claim 14, wherein the image acquisition apparatus comprises at least one of a computed tomography (CT) system, a C-arm CT system, and a tomosynthesis system.

17. The method of claim 14, further comprising training the neural network via a training process with a greedy reward function, which includes an image quality term and a dose-constraint term,
  wherein the image quality term, at each iteration of the training process, includes a difference between ground truth volume data, determined from the particular task information and/or the test scan data, and particular volume data obtained at the iteration of the training process.

18. The method of claim 17, further comprising generating the particular volume data at each iteration of the training process via reconstruction of simulated projections, which are obtained from the ground truth volume data and based on system geometry.

19. The method of claim 17, wherein the neural network is trained via the training process, which includes applying a mask to regions of interest based on the particular task information and/or the test scan data.

20. The method of claim 14, wherein the first set of imaging conditions include exposure parameters, which are at least one of an angle, a dose, or an energy value.

21. The method of claim 14, further comprising:
  receiving the particular task information and/or the test scan data, and
  storing, in a memory, a data structure associating, for each network identifier of a plurality of neural network identifiers, a corresponding set of task information and/or test scan data,
  wherein the obtaining step further comprises determining a particular network identifier identifying the trained neural network, based on the stored data structure and the received particular task information and/or the test scan data.

* * * * *